(12) United States Patent
Olbert et al.

(10) Patent No.: US 8,558,026 B2
(45) Date of Patent: Oct. 15, 2013

(54) METHOD FOR PRODUCING ISOCYANATES

(75) Inventors: Gerhard Olbert, Dossenheim (DE);
Torsten Mattke, Freinsheim (DE);
Carsten Knoesche, Niederkirchen (DE);
Andreas Daiss, Deidesheim (DE); Jens Denecke, Speyer (DE)

(73) Assignee: BASF SE, Ludwigshafen (DE)

( * ) Notice: Subject to any disclaimer, the term of this patent is extended or adjusted under 35 U.S.C. 154(b) by 648 days.

(21) Appl. No.: 12/675,187

(22) PCT Filed: Aug. 13, 2008

(86) PCT No.: PCT/EP2008/060630
§ 371 (c)(1),
(2), (4) Date: Feb. 25, 2010

(87) PCT Pub. No.: WO2009/027232
PCT Pub. Date: Mar. 5, 2009

(65) Prior Publication Data
US 2010/0210870 A1 Aug. 19, 2010

(30) Foreign Application Priority Data
Aug. 30, 2007 (EP) ..................................... 07115316

(51) Int. Cl.
*C07C 263/00* (2006.01)

(52) U.S. Cl.
USPC ......................................................... 560/347

(58) Field of Classification Search
None
See application file for complete search history.

(56) References Cited

U.S. PATENT DOCUMENTS

| | | | |
|---|---|---|---|
| 6,225,497 B1 * | 5/2001 | Becker et al. | 560/347 |
| 6,930,199 B2 * | 8/2005 | Meyn et al. | 560/347 |
| 6,974,880 B2 * | 12/2005 | Biskup et al. | 560/347 |
| 2003/0013909 A1 | 1/2003 | Leimkuhler et al. | |
| 2003/0216597 A1 * | 11/2003 | Jenne et al. | 560/347 |
| 2004/0091406 A1 * | 5/2004 | Wolfert et al. | 422/224 |
| 2005/0113601 A1 * | 5/2005 | Herold et al. | 560/347 |
| 2009/0054684 A1 * | 2/2009 | Stutz et al. | 560/347 |
| 2009/0221846 A1 * | 9/2009 | Wolfert et al. | 560/347 |
| 2009/0281350 A1 | 11/2009 | Knoesche et al. | |
| 2010/0041914 A1 * | 2/2010 | Woelfert et al. | 560/347 |
| 2010/0048942 A1 | 2/2010 | Knoesche et al. | |

FOREIGN PATENT DOCUMENTS

| | | | |
|---|---|---|---|
| DE | 300168 | * | 5/1992 |
| DE | 102 60 092 | | 7/2004 |
| DE | 103 59 627 | | 7/2005 |
| DE | 10 2005 042 392 | | 3/2007 |
| EP | 0 289 840 | | 11/1988 |
| EP | 0 570 799 | | 11/1993 |
| EP | 0 593 334 | | 4/1994 |
| EP | 1 275 639 | | 1/2003 |
| EP | 1 275 640 | | 1/2003 |
| EP | 1 319 655 | | 6/2003 |
| EP | 1 362 847 | | 11/2003 |
| EP | 1 403 248 | | 3/2004 |

(Continued)

OTHER PUBLICATIONS

Derwent Abstract for 300168.*

(Continued)

*Primary Examiner* — Karl J Puttlitz
(74) *Attorney, Agent, or Firm* — Oblon, Spivak, McClelland, Maier & Neustadt, L.L.P.

(57) ABSTRACT

The present invention relates to a process for preparing isocyanates.

17 Claims, 5 Drawing Sheets

(56) References Cited

FOREIGN PATENT DOCUMENTS

| | | | |
|---|---|---|---|
| EP | 1 449 826 | | 8/2004 |
| EP | 1 526 129 | | 4/2005 |
| GB | 2036586 | * | 7/1980 |
| WO | 03 045900 | | 6/2003 |
| WO | 2004 026813 | | 4/2004 |
| WO | 2005 123665 | | 12/2005 |
| WO | 2008 055895 | | 5/2008 |
| WO | 2008 055899 | | 5/2008 |
| WO | 2008 055904 | | 5/2008 |

OTHER PUBLICATIONS

U.S. Appl. No. 12/918,942, filed Aug. 23, 2010, Grossschmidt, et al.
U.S. Appl. No. 12/675,137, filed Feb. 25, 2010, Olbert, et al.
U.S. Appl. No. 12/678,771, filed Mar. 18, 2010, Knoesche, et al.
U.S. Appl. No. 13/001,681, filed Dec. 28, 2010, Knoesche, et al.

* cited by examiner

METHOD FOR PRODUCING ISOCYANATES

CROSS-REFERENCE TO RELATED APPLICATIONS

This application is a National Stage of PCT/EP2008/060630 filed on Aug. 13, 2008. This application is based upon and claims the benefit of priority to European Application No. 07115316.7 filed on Aug. 30, 2007.

BACKGROUND OF THE INVENTION

The present invention relates to a process for preparing isocyanates.

To prepare isocyanates by phosgenating the corresponding amines, there is in principle the possibility of a liquid phase phosgenation or of a gas phase phosgenation. In the gas phase phosgenation, the reaction conditions are selected such that at least the diamine, diisocyanate and phosgene reaction components, but preferably all reactants, products and reaction intermediates, are gaseous under these conditions, more preferably until the reaction is complete. The present invention relates exclusively to gas phase phosgenation. In this context, "essentially" means to an extent of at least 50% by weight based on all reaction components, preferably to an extent of at least 66%, more preferably to an extent of at least 75%, even more preferably to an extent of at least 85%, in particular to an extent of at least 90% and especially to an extent of at least 95%. The temporary formation of liquid droplets and/or temporarily formed particulate solids which react in a gaseous environment would be conceivable.

EP 1 275 639 A1 describes the gas phase phosgenation of (cyclo)aliphatic diamines in a reaction zone with constrictions of the walls.

In the mixing device, the amine- and phosgene-containing reactant streams are fed coaxially to a mixing zone, the phosgene-containing reactant stream being conducted in the interior and the amine-containing reactant stream in the exterior. In the region in which the reactant streams are combined, i.e. the reaction zone, there is a further reduction or slight enlargement of the flow cross section, such that the flow rate rises owing to the volume increase in the course of the reaction as a result of expansion of the gas.

A disadvantage of this arrangement is that the amine stream is conducted coaxially in the exterior. This can result in solid formation on the walls of the mixing device, since the amine is present in excess compared to the phosgene at the walls, which promotes by-product formation.

It is likewise stated in EP 1275639A1 that swirling of the reactant streams should be effected in the mixing apparatus before the reactant streams are combined such that the turbulent variable speeds in the reactant flows are then increased and the mixing is then effected more rapidly when the two reactant streams are combined.

EP 1526129 A1 describes the increase in turbulence in a mixing nozzle by swirl-generating internals. This generates tangential vortexing of the overall stream, which does not, however, have a significant effect on the mixing of the different streams with one another.

EP 1 275 640 A1 describes the gas phase phosgenation of (cyclo)aliphatic di- and triamines in a mixing tube with a reactor, in which the gas flow in the mixing region is accelerated.

A disadvantage of this process is that the maximum speed difference between the reactant streams is not achieved immediately at the start of mixing, and hence the minimum possible mixing time is not achieved either.

DE 10359627 A1 discloses a gas phase phosgenation in which amine is mixed in by means of a concentric ring gap between two phosgene streams, where the areas through which the phosgene streams flow are in a ratio of from 1:0.5 to 1:4.

International application WO 2007/028715 discloses a process in which amine and phosgene are metered in through an annular gap, i.e. a ring-shaped continuous gap.

In all of these documents, exclusively smooth nozzles are disclosed; turbulence-generating internals are disclosed at best by means of twisted arrangements.

None of the mixing apparatus known in the prior art cited has to date had the effect of permanently and satisfactorily suppressing the formation of solids at the point of combination of the amine stream and of the phosgene stream.

It was thus an object of the present invention to develop a reaction regime for a gas phase phosgenation, with which industrial scale performance is possible and which becomes insusceptible to blockages by virtue of there being only a small tendency to deposit solids.

BRIEF SUMMARY OF THE INVENTION

The object is achieved by processes for preparing isocyanates by reacting the corresponding amines with phosgene in the presence of at least one, preferably exactly one, inert medium in the gas phase, by contacting fluid streams of amine, phosgene and inert medium in at least one mixing device and then reacting amine and phosgene with one another, which comprises metering in an inert medium at least between one amine stream and one phosgene stream in the mixing device.

The present invention further provides for the use of three-substance mixing nozzles for metered addition of fluid streams of amine, phosgene and inert medium in gas phase phosgenation.

The present invention further provides for the use of three-substance mixing nozzles for metered addition of fluid streams of amine, phosgene and inert medium in liquid phase phosgenation.

DETAILED DESCRIPTION OF THE INVENTION

This inventive principle can be applied generally to procedures in which rapid mixing of fluid, i.e. gaseous or liquid, substances is desired, especially in chemical reactions.

Such chemical reactions are preferably those in which solid substances are formed as end products or intermediates under the reaction conditions. The cause of the solids formation is local oversaturation of the solid-forming component with respect to the equilibrium solubility. The more rapid the mixing, the higher the oversaturation is too. Relatively high oversaturation leads to the formation of more solid nuclei and generally to smaller primary particles. When this is an intermediate, small primary particles react further more rapidly than large primary particles, since they have more surface area. The rate of the subsequent reaction thus depends crucially on the size of the particles formed. For high space-time yields, very small particles therefore have to be generated in the mixing unit. Moreover, the formation of relatively large particles leads to the risk of formation of deposits in the mixing unit. To prevent solid deposits and to achieve short mixing times, small interface layers are therefore the aim.

This principle is applicable both to monophasic and polyphasic, mutually miscible or immiscible media.

Advantageously, the inventive apparatus can be used in the preparation of isocyanates by reacting the corresponding amines with phosgene, as a mixing apparatus for the mixing of amine and phosgene. It is at first unimportant whether the reaction takes place in the gas phase or in the liquid phase; it may particularly advantageously be used as a mixing apparatus in the gas phase phosgenation.

For example, EP 289840 B1 and EP 1275639 A1 disclose the mixing of amine and phosgene in the gas phase phosgenation with the aid of a combination of nozzle and annular gap. This mixing principle is shown by way of example in FIG. 1.

It has now been found that, by virtue of metering in an inert medium in the mixing device for mixing fluid streams of amine, phosgene at least between one amine stream and one phosgene stream, the deposition of blocking solids in the region of the mixing device can be reduced to suppressed.

Figure 1:
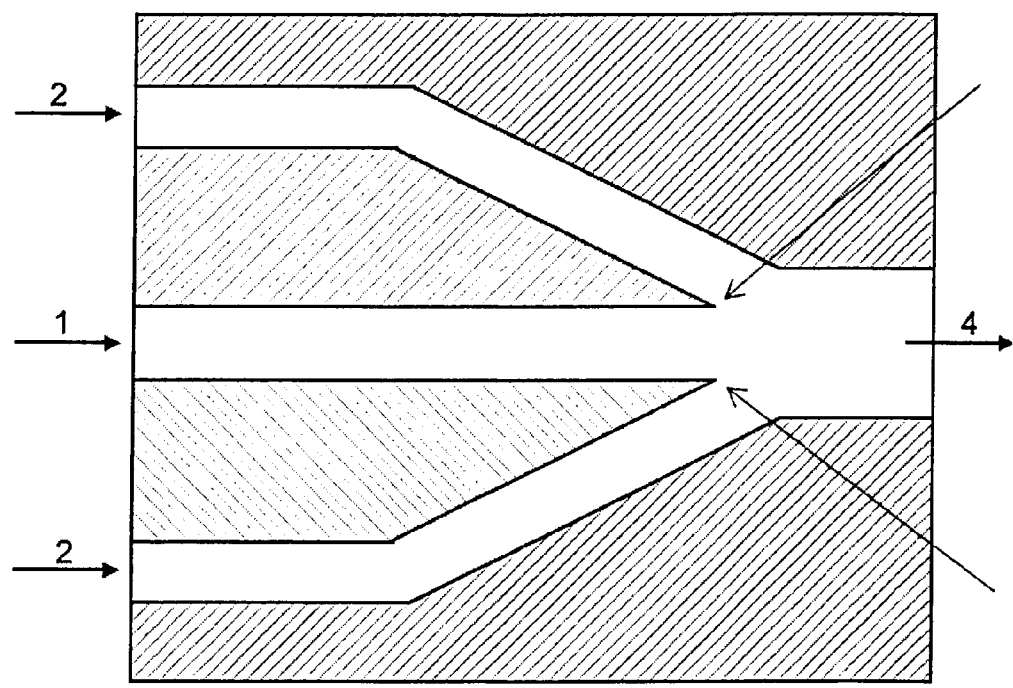
FIG. 1 depicts an example of a known mixing device.

The greatest tendency for solids to be precipitated arises in mixing devices according to FIG. 1 at the point of first contact of amine stream and phosgene stream (see unlabeled arrows). The cause of this may be displacements of the flow (recirculation areas) at the point of contact, or else the area of superimposition of the interface layers of the feeds at the point of contact. In these zones, the residence time is increased. Phosgene and amine react to give isocyanates which can react further to give solid conversion products such as ureas, diimides or cyanurates. These may be deposited in the region of the point of contact and lead to deposit formation in the mixing unit.

By virtue of the inventive metered addition of an inert medium between the streams of phosgene and amine, contact between the two reacting streams close to the wall is prevented. The mixing is thus effected at a distance from the wall, such that lower deposit formation is the consequence.

Figure 2:
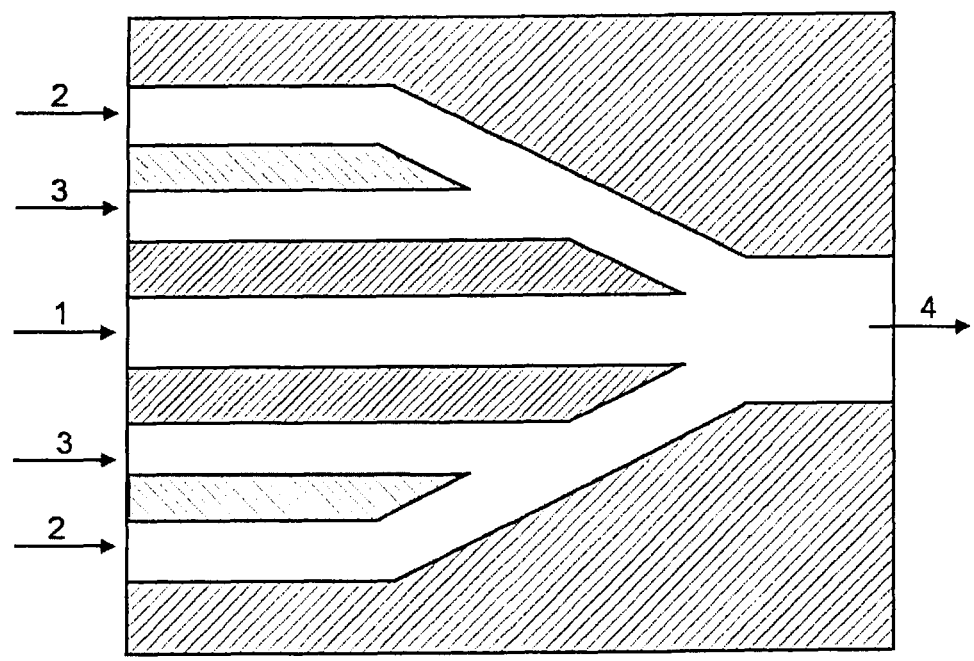
FIGS. 2-5 depict different embodiments falling with the scope of the present invention.

One embodiment of the present invention is shown in FIG. 2: In this embodiment, an inner amine stream 1 is metered in between two phosgene streams 2 in a mixing device. According to the invention, on the inner side, i.e. on the side of the phosgene stream channels 2 facing the amine stream 1, an inert medium 3 is metered in in each case such that complete mixing of phosgene and inert medium does not occur up to the opening point of the channel for the amine. In this case, the phosgene concentration at the opening point of the amine is lowered and is ideally 0. In this case, at the opening point, only amine and inert medium are present, and the formation of solid conversion products can be prevented.

The distance of the inert metering point into the phosgene channel from the opening point of the amine stream should be selected such that, up to there, complete mixing of inert medium and phosgene has not occurred. As is well known, the mixing length in turbulent flow is about 50 times the hydraulic diameter of the channel dimension. Accordingly, the distance of the inert metering point from the amine opening point should be less than 50 times the hydraulic diameter of the phosgene feed at the opening point, preferably less than 10 times and more preferably less than 5 times.

The ratio of the absolute speeds of inert medium and phosgene at the point of contact of the two flows should, to prevent excessively rapid mixing, be in the range from 2:1 to 1:2, preferably from 1.5:1 to 1:1.5 and more preferably from 1.2:1 to 1:1.2.

The speed difference of the absolute speeds of inert medium and phosgene is preferably less than 10 m/s, more preferably less than 8 m/s and most preferably less than 5 m/s.

Figure 3:
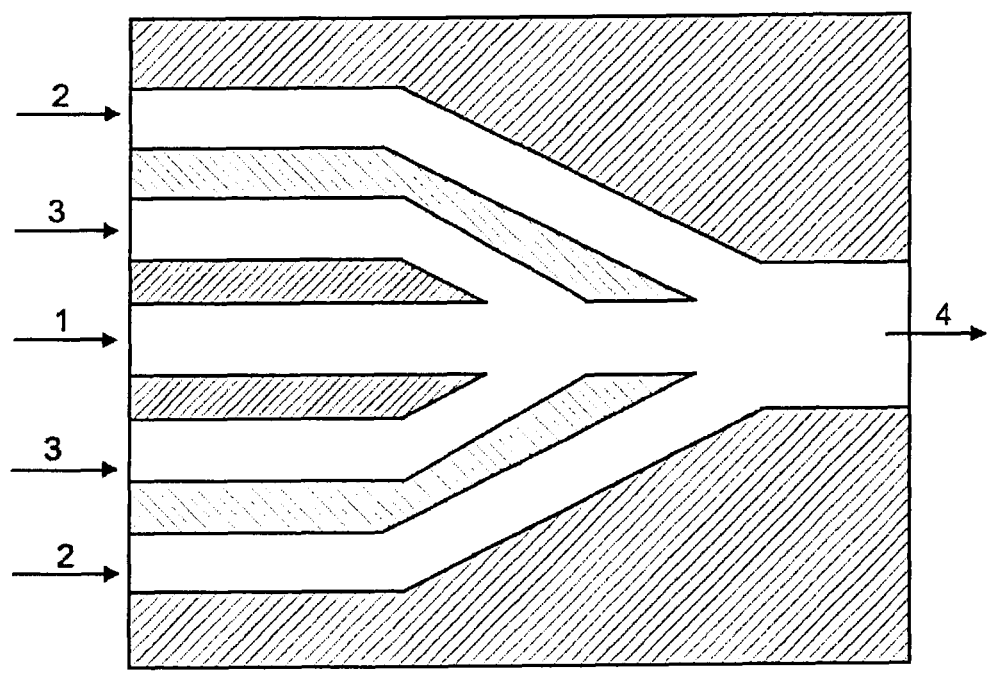

A further embodiment of the present invention is shown in FIG. 3: In this embodiment, in a mixing device, an inner amine stream 1 is metered in between two phosgene streams 2. According to the invention, on the outer side, i.e. on the side of the amine flow channel 1 facing the phosgene stream 2, an inert medium 3 is metered in in each case such that, up to the opening point of the amine channel, complete mixing of amine and inert medium does not occur. In this case, the amine concentration at the opening point of the phosgene channel 2 is lowered and is ideally 0. In this case, only phosgene and inert medium are present at the opening point, and the formation of solid conversion products can be prevented.

The distance of the inert metering point into the amine channel 1 from the opening point of the phosgene stream 2 should be selected such that, up to there, complete mixing of inert medium and amine has not occurred. The distance of the inert metering point from the phosgene opening point should be less than 50 times the hydraulic diameter of the amine feed at the opening point, preferably less than 10 times and more preferably less than 5 times.

The ratio of the absolute speeds of inert medium and amine at the point of contact of the two flows should, to prevent excessively rapid mixing, be in the range from 2:1 to 1:2, preferably from 1.5:1 to 1:1.5 and more preferably from 1.2:1 to 1:1.2.

Figure 5:
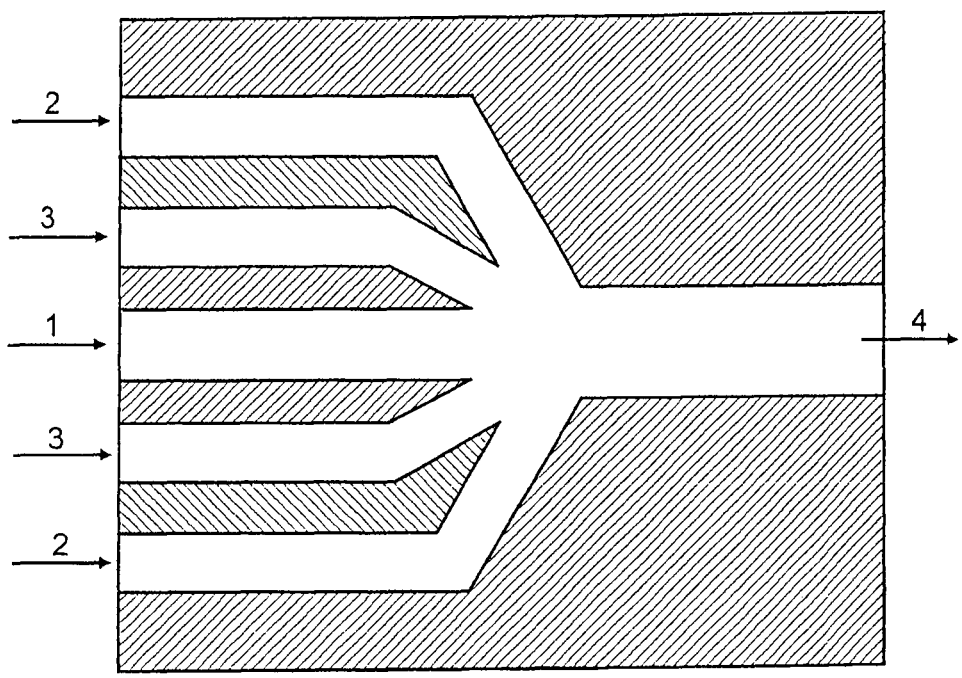

A further preferred embodiment of the present invention is shown in FIG. 5: In this embodiment, in a mixing device, an inner amine stream 1 is metered in between two phosgene streams 2. According to the invention, one inert medium 3 is metered in each case between the phosgene channel 2 and the amine stream channel 1. This initially brings about a spatial separation of amine stream 1 and phosgene stream 2, such that only amine and inert medium come into contact at the opening point of the amine channel 1, and only phosgene and inert medium at the opening points of the phosgene channels 2.

Figure 4:
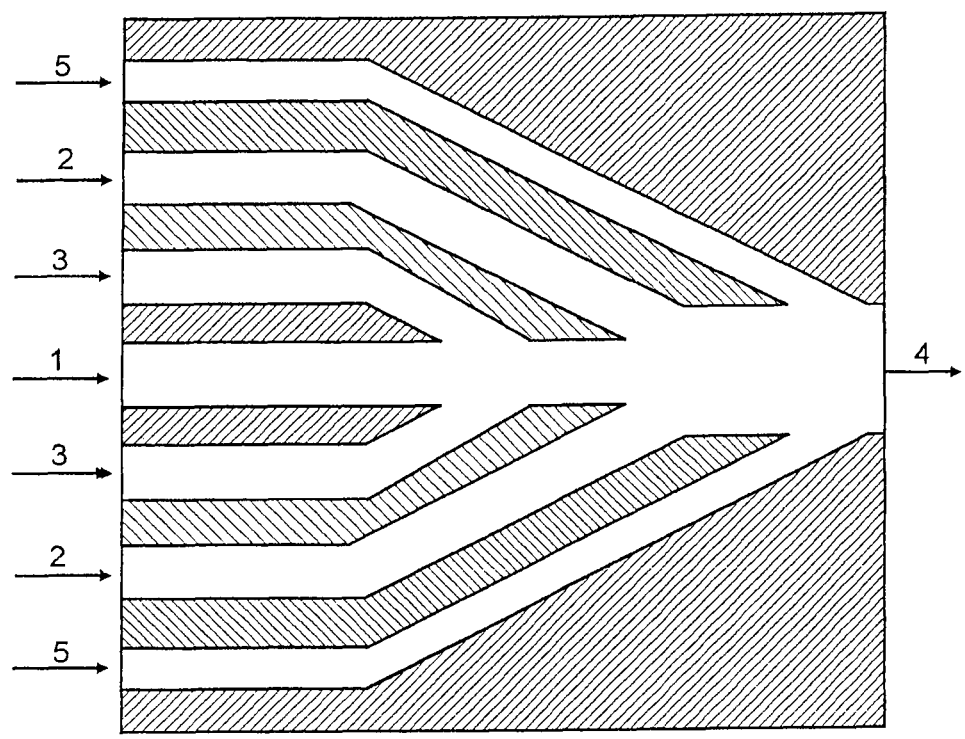

In addition to this inventive separation of amine stream and phosgene stream by an inert medium, it is optionally also possible to meter in an inert stream between the wall and the outer phosgene stream, as shown by way of example in FIG. 4: To this end, a further stream 5 of an inert medium is metered in between phosgene stream 2 and wall, while an inert medium 3 can be metered in between amine stream 1 and phosgene stream 2, as in the embodiments of FIG. 1, 2 or 5.

The effect of this is to keep the reaction mixture away from the wall, such that any solids formed as an intermediate can be deposited on the wall of the reaction chamber only to a reduced degree, if at all.

In this context, the distance of the metering point of the inert medium 5 into the channel of the reaction mixture 4 from the point of combination with the phosgene stream 2 plays a minor role, provided that the reaction mixture is kept away from the wall.

Such a metered addition of an inert stream between the wall and reaction mixture can be effected once or more than once, for example at from one to four points in the reaction chamber, preferably at from one to three points, more preferably at from one to two points and most preferably at one point.

Such a metered addition of an inert stream between the wall and reaction mixture makes sense especially for the points in the reaction chamber at which amine and phosgene are only partly converted with respect to the deficiency components, for example at a partial conversion up to 85%, preferably up to 75%, more preferably up to 50%, even more preferably up to 30% and in particular up to 15%. In these regions, the risk of solids formation is particularly high, since hydrogen chloride released in the course of the reaction can react with free amine and can thus form solid particles which can precipitate. Apart from these amine hydrochlorides, conversion products of amine and isocyanate or of isocyanates with one another, for example ureas, diamides or isocyanurates, can lead to deposits, whose formation can be reduced by the inventive procedure.

It is also conceivable, albeit less preferred, to conduct the present invention merely with one metered addition of an inert medium 5 between the wall and reaction mixture 4 without metered addition of an inert medium 3 between phosgene stream 2 and amine stream 1.

The mixing device may preferably be a static mixing unit, for example a nozzle mixing device, for example coaxial mixing nozzles, Y or T mixers, jet mixers or mixing tubes.

In a coaxial mixing nozzle, one component (preferably the amine) is conducted into the other component (which is then preferably phosgene) at high speed through a concentric tube with a small diameter (nozzle) in a mixing tube.

The reactors may, for example, be cylindrical reaction spaces without internals and without moving parts.

One embodiment of a mixing/reaction unit is described in EP 1275639 A1, and there particularly in paragraphs [0013] to [0021] and the example together with FIG. 1, which is hereby incorporated in the present disclosure by reference. Preference is given, however, in contrast to the disclosure there, to the metered addition of the amine through the internal tube and of phosgene as the outer stream.

One embodiment of a mixing/reaction unit is described in EP 1275640 A1, and there particularly in paragraphs [0010] to [0018] and the example together with FIG. 1, which is hereby incorporated in the present disclosure by reference. Preference is given, however, in contrast to the disclosure there, to the metered addition of the amine through the internal tube and of phosgene as the outer stream.

A further embodiment of a mixing/reaction unit is described in EP 1319655 A2, and there particularly in paragraphs [0015] to [0018] and the example together with FIG. 1, which is hereby incorporated into the present disclosure by reference.

It may be advisable to install flow homogenizers, as described in EP 1362847 A2, and there particularly in paragraphs [0008] to [0026] and the example together with FIG. 1, which is hereby incorporated in the present disclosure by reference.

Also conceivable is the use of a plurality of nozzles aligned in parallel, as described in EP 1449826 A1, and there particularly in paragraphs [0011] to [0027] and example 2 together with FIGS. 1 to 3, which is hereby incorporated in the present disclosure by reference.

A further embodiment of a mixing/reaction unit is described in DE 10359627 A1, and there particularly in paragraphs [0007] to [0025] and example 1 together with the figure, which is hereby incorporated in the present disclosure by reference.

A preferred embodiment of a mixing nozzle is a slot mixing nozzle, as described in WO 2008/55895, and there particularly from page 3 line 26 to page 15 line 31, and a reaction chamber as described there from page 15 line 35 to page 23 line 31, together with the figures, which is hereby incorporated in the present disclosure by reference.

The mixing device is preferably a slot mixing nozzle having an odd number of slots, for example 5, 7, 9, etc.

In such slotted stacks, the individual streams can be metered in, for example, in the following sequence:

Phosgene-[-inert medium-amine-inert medium-phosgene-]$_n$ where n≥1 or

Inert-phosgene-[-inert-amine-inert-phosgene-]$_n$-inert where n≥1 n may preferably assume values of 1 or 2, more preferably of 1.

A particularly preferred embodiment of a mixing nozzle is an annular gap mixing nozzle, as described in international patent application WO 2007/028715, and there particularly from page 2 line 23 to page 11 line 22, and a reaction chamber as described there from page 11 line 26 to page 21 line 15 together with FIG. 2, which is hereby incorporated in the present disclosure by reference.

The mixing device is preferably an annular gap mixing nozzle having an odd number of annular gaps, for example 5, 7, 9, etc.

The sequence of metered addition may be analogous to that specified for the slotted stacks.

When no inert medium stream 5 is metered in between the phosgene stream 2 and wall, it is advantageous to prevent solid deposition and blockages in the inventive mixing device preferably by conducting the phosgene-containing reactant stream such that all apparatus walls, after combination of the reactant streams, are flowed over by the phosgene-containing reactant stream(s), and the amine-containing reactant stream(s) is/are enveloped completely by the phosgene-containing reactant stream(s) until there is complete mixing of the streams or substantially complete conversion of the amine.

Preference is therefore given to metering in the amine on the inside, such that the stream is surrounded completely on all sides by a phosgene stream. Conceivable, albeit less preferred, is a metered addition in which phosgene is metered in on the inside and amine on the outside. In this case, preference is given to metering in an inert medium between the wall and the amine.

The amines which can be used in a gas phase phosgenation have to satisfy particular requirements (see below).

The amines may be monoamines, diamines, triamines or higher-functionality amines, preferably diamines. This accordingly gives rise to the corresponding monoisocyanates, diisocyanates, triisocyanates or higher-functionality isocyanates, preferably diisocyanates.

The amines and isocyanates may be aliphatic, cycloaliphatic or aromatic, preferably aliphatic or cycloaliphatic and more preferably aliphatic.

Cycloaliphatic isocyanates are those which comprise at least one cycloaliphatic ring system.

Aliphatic isocyanates are those which have exclusively isocyanate groups which are bonded to straight or branched chains.

Aromatic isocyanates are those which have at least one isocyanate group bonded to at least one aromatic ring system.

In the context of this application, (cyclo)aliphatic isocyanates are an abbreviated representation of cycloaliphatic and/or aliphatic isocyanates.

Examples of aromatic diisocyanates are preferably those having 6-20 carbon atoms, for example monomeric methylene 2,4'- or 4,4'-di(phenyl isocyanate) (MDI), tolylene 2,4- and/or 2,6-diisocyanate (TDI) and naphthyl 1,5- or 1,8-diisocyanate (NDI).

Diisocyanates are preferably (cyclo)aliphatic diisocyanates, more preferably (cyclo)aliphatic diisocyanates having from 4 to 20 carbon atoms.

Examples of customary diisocyanates are aliphatic diisocyanates such as tetramethylene 1,4-diisocyanate, pentamethylene 1,5-diisocyanate, hexamethylene diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, derivatives of lysine diisocyanate, tetramethylxylylene diisocyanate (TMXDI), trimethylhexane diisocyanate or tetramethylhexane diisocyanate, and also 3 (or 4), 8 (or 9)-bis(isocyanatomethyl)-tricyclo[$5.2.1.0^{2,6}$]decane isomer mixtures, and also cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(isocyanatomethyl)cyclohexane, 2,4- or 2,6-diisocyanato-1-methylcyclohexane.

Preference is given to pentamethylene 1,5-diisocyanate, 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures. Particular preference is given to 1,6-diisocyanatohexane, 1-isocyanato-3,3,5-trimethyl-5-(isocyanatomethyl)-cyclohexane and 4,4'-di(isocyanatocyclohexyl)methane.

For the process according to the invention, it is possible to use those amines for the reaction to give the corresponding isocyanates for which the amine, its corresponding intermediates and the corresponding isocyanates are present in gaseous form under the selected reaction conditions. Preference is given to amines which, during the reaction, decompose under the reaction conditions to an extent of at most 2 mol %, more preferably to an extent of at most 1 mol % and most preferably to an extent of at most 0.5 mol %. Particularly suitable here are amines, especially diamines, based on aliphatic or cycloaliphatic hydrocarbons having from 2 to 18 carbon atoms. Examples thereof are 1,5-diaminopentane, 1,6-diaminohexane, 1-amino-3,3,5-trimethyl-5-aminomethylcyclohexane (IPDA) and 4,4'-diaminodicyclohexylmethane. Preference is given to using 1,6-diaminohexane (HDA).

It is likewise possible to use aromatic amines for the process according to the invention, which can be converted to the gas phase without significant decomposition. Examples of preferred aromatic amines are tolylenediamine (TDA), as the 2,4- or 2,6-isomer or as a mixture thereof, for example as an 80:20 to 65:35 (mol/mol) mixture, diaminobenzene, 2,6-xylidine, napthyldiamine (NDA) and 2,4'- or 4,4'-methylene-(diphenylamine) (MDA) or isomer mixtures thereof. Among these, preference is given to the diamines, particular preference to 2,4- and/or 2,6-TDA.

In the gas phase phosgenation, the aim is by definition that the compounds which occur in the course of the reaction, i.e. reactants (diamine and phosgene), intermediates (especially the mono- and dicarbamyl chlorides which form as intermediates), end products (diisocyanate), and any inert compounds metered in, remain in the gas phase under the reaction conditions. Should these or other components be deposited out of the gas phase, for example on the reactor wall or other apparatus components, these depositions can undesirably change the heat transfer or the flow of the components in question. This is especially true of amine hydrochlorides which form from free amino groups and hydrogen chloride (HCl), since the resulting amine hydrochlorides precipitate out readily and are only reevaporable with difficulty.

The reactants, or else only one of them, in addition to the additional metered addition of an inert medium according to the invention, may be metered into the mixing chamber diluted with at least one inert medium.

The inert medium is a medium which is present in the reaction chamber in gaseous form at the reaction temperature and does not react significantly with the compounds which occur in the course of the reaction. What is meant by this is that less than 10 mol % of the inert medium reacts chemically under the reaction conditions, preferably less than 5 mol %, more preferably less than 3 mol % and most preferably less than 1 mol %.

The inert medium is generally mixed with amine and/or phosgene before the reaction, but may also be metered in separately from the reactant streams. For example, nitrogen, noble gases such as helium or argon, or aromatics such as chlorobenzene, chlorotoluene, o-dichlorobenzene, toluene, xylene, chloronaphthalene, decahydronaphthalene, carbon dioxide or carbon monoxide may be used. Preference is given to using nitrogen and/or chlorobenzene as the inert medium.

In general, the inert medium is used in an amount such that the ratio of the gas volumes of inert medium to amine or to phosgene is less than 1, preferably less than 0.1 and more preferably less than 0.05.

Before the process according to the invention is carried out, the starting amines are evaporated and heated to from 200° C. to 600° C., preferably from 300° C. to 500° C., and fed to the reactor through the mixing device, if appropriate diluted with an inert gas or with the vapors of an inert solvent.

Before performing the process according to the invention, the phosgene used in the phosgenation is likewise heated to a temperature within the range from 200° C. to 600° C., preferably from 300° C. to 500° C., if appropriate diluted with an inert gas or with the vapors of an inert solvent.

According to the invention, phosgene is used in excess based on amino groups. Typically, a molar ratio of phosgene to amino groups of from 1.1:1 to 20:1, preferably from 1.2:1 to 5:1 is present.

The mixing and reaction of the two gaseous reactants takes place in the process according to the invention after the introduction of the diamine and phosgene reactant streams and also inert medium, via the slots as entry areas, in the mixing chamber as the reaction chamber.

The reaction generally sets in with contact of the reactants immediately after the mixing.

Thus, the mixing of the reactants, if appropriate mixed with inert medium, takes place in the front part of the reaction chamber (mixing chamber).

To perform the inventive reaction, the preheated stream comprising amine or mixtures of amines and the preheated stream comprising phosgene are passed continuously into the reactor, preferably a tubular reactor.

The reactors consist generally of steel, glass, alloyed or enameled steel, and have a length which is sufficient to enable full reaction of the diamine with the phosgene under the process conditions.

It may be advisable to incorporate flow homogenizers into the reactant lines, as known, for example, from EP 1362847A. For homogenization of the speed of the reactant streams, however, preference is given to a long initial length in the reactant line relative to the diameter of the feed line, which is from 2 to 40 times the feed line diameter, more preferably from 4 to 30 times, most preferably from 5 to 20 times.

A constriction of the flow cross section as described in patent EP 1275640A1 after the combination of the reactant streams to prevent backflows is possible, but preference may be given to dispensing with one.

Following the concept of the invention, in order that an amine stream, after the start of mixing, has no contact with the apparatus walls but rather is surrounded by phosgene-containing reactant streams, the amine stream is metered in between phosgene streams. In addition, the apparatus walls can be protected by an additional stream 5 of an inert medium.

The flow cross sections of the phosgene-containing reactant stream(s) is/are configured such that the characteristic mixing length measure again becomes as small as possible. Since the phosgene reactant is supplied in stoichiometric excess and, moreover, the phosgene speed is preferably less than the amine speed, a greater cross-sectional area has to be selected than for the amine-containing stream, which also gives rise to greater characteristic dimensions. The mixing path length is selected at less than 200 mm, preferably less than 100 mm, more preferably less than 50 mm, even more preferably less than 25 mm and especially less than 10 mm. The mixing path length is defined as the maximum distance that the fluid elements of two or more reactant streams have to pass through at right angles to the flow direction of the reactant streams until molecular mixing of the reactant streams has been effected.

The ratio of the total area of the amine streams to the total area of the phosgene streams is greater than 0.00002, preferably greater than 0.0002, more preferably greater than 0.002 and most preferably greater than 0.02.

The ratio of the total area of the amine streams to the total area of the phosgene streams is less than 5, preferably less than 1, more preferably less than 0.5 and most preferably less than 0.2.

The area ratio of two phosgene-conducting areas separated by an amine-conducting slot is from 0.1 to 10, preferably from 0.2 to 5, more preferably from 0.4 to 2.5, very particularly from 0.8 to 1.25, in particular from 0.9 to 1.1 and especially 1.

The ratio of the area of an inert medium stream to the total area of the adjacent amine stream and phosgene stream is greater than 0.0002, preferably greater than 0.002 and more preferably greater than 0.02, and is up to 5, preferably up to 2 and more preferably up to 1.

Since the intensity and rapidity of the mixing of the amine- and phosgene-containing reactant streams depend significantly on the shear gradient to be established in the mixing zone, the mixing zone has to be configured such that the shear gradient is particularly high.

To this end, the speed difference between the amine- and phosgene-containing reactant streams should firstly be selected at a particularly high level and the characteristic length dimensions should be selected at a minimum level, since the shear gradient is proportional to the quotient of speed difference and characteristic length dimension.

The speed difference between the stream of the inert medium and the adjacent stream should not, however, be so great that an extensive recirculation area is formed by the entering jet.

Since the speed difference between the amine- and phosgene-containing reactant streams should be high, either the phosgene-containing or the amine-containing reactant streams must have a high speed. Since the amine feeds to the mixing zone are relatively sensitive to the formation of deposits and blockages and backflow in the amine feed should be avoided in any case, the flow rate of the amine-containing reactant stream is preferably selected to be greater than the speed of the phosgene-containing reactant stream.

The higher the speed of the amine-containing reactant streams, the higher the speed of the phosgene-containing reactant streams can also be selected at the same shear rate. A higher phosgene speed brings about smaller flow cross sections of the phosgene feed and hence smaller mixing path lengths and hence more rapid mixing.

In order to achieve a very high amine speed, the aim is therefore to establish a local Mach number of greater than 0.6 in the amine stream at the point of combination with the phosgene stream.

The Mach number means the ratio between local flow rate and local speed of sound. In a particular embodiment of the process, feed rate of the amine-containing reactant streams is selected such that exactly a Mach number of 1 is present at the exit of the amine streams into the mixing zone.

In the case of an adjusted amine feed rate, the pressure of the amine stream at this point corresponds exactly to the pressure of the phosgene-containing reactant stream at the point of combination. In the case of an unadjusted amine feed rate, the pressure of the amine stream at the exit from the amine feed is greater than the pressure of the phosgene-containing stream at the combination. In this case, there is then further expansion of the amine-containing stream, which is associated with a pressure drop down to the pressure of the phosgene-containing stream.

Whether a nozzle is operated adjusted or unadjusted depends on the upstream pressure of the amine-containing stream and of the phosgene-containing stream upstream of the mixing nozzle.

In a further particular embodiment, the amine feed rate is configured such that Mach numbers of greater than 1 are achieved actually in the feeds. This can be achieved, for example, by configuring the feed of the amine-containing streams in the form of one or more Laval nozzles, which feature initial narrowing of the flow cross section until a Mach number of one is attained and then widening again, which leads to a further expansion and acceleration of the flow. In order to achieve supersonic flow (Mach number greater than 1), the ratio of the amine tank pressure to the mixing zone pressure must be greater than the so-called critical pressure ratio. The higher the pressure ratio and the higher the tank temperature of the amine stream, the higher is the maximum achievable speed.

Since the amine reactant is often damaged thermally at excessively high temperatures, however, no excessively high temperatures can be established. The upstream amine pressure also cannot be increased as desired owing to the amine vapor pressure. Preference is therefore given to configuring the amine feed such that, in the amine-containing reactant stream, directly at the combination with the phosgene-containing stream, or, in the case of an unadjusted nozzle, just downstream thereof, Mach numbers of from 0.6 to 4, more preferably from 0.7 to 3, even more preferably from 0.8 to 2.5 and especially from 0.9 to 2.0 are established.

The Mach numbers specified can be converted by the person skilled in the art to flow rates in a simple manner with a known tank temperature and known substance data. Equally, the person skilled in the art can calculate the upstream pressure required depending on the given Mach number and the substance data.

The high entry speed of the amine stream into the mixing zone serves, as stated above, to achieve a very large speed difference between amine-containing and phosgene-containing reactant streams. Moreover, the high flow rate locally reduces the system pressure and hence also the reactant concentrations and the temperature, which leads to a reduction in the reaction rates and hence to a simplification of the mixing task.

In order to achieve very short mixing path lengths, the aim must be likewise to select the flow rate of the phosgene-containing reactant stream at as high as possible a level, but without too greatly reducing the speed difference between amine-containing and phosgene-containing reactant stream. To this end, the cross-sectional area of the phosgene stream is selected so as to give rise to a Mach number of from 0.2 to 2.0, preferably from 0.3 to 1.5, more preferably from 0.4 to 1.0, even more preferably from 0.5 to 1.0 and especially from 0.7 to 1.0.

The flow cross sections of the amine-containing reactant streams are configured in the inventive mixing unit such that, firstly, a high operational stability is ensured and, otherwise, very short mixing path lengths are maintained. Therefore, length dimensions characteristic for the supply of the amine-containing reactant stream of from 0.5 to 50 mm, preferably from 0.75 to 25 mm, more preferably from 1 mm to 10 mm and most preferably from 1 mm to 5 mm are selected. The characteristic length dimension means the smallest length measure of the flow cross section, i.e., in the case of a gap, the gap width, or, in the case of a circular orifice, the orifice diameter.

The individual reactants in the mixing device are preferably conducted into the reactor with a flow rate of from 20 to 400 meters/second, preferably from 25 to 300 meters/second, more preferably from 30 to 250 meters/second, even more preferably from 50 to 200 meters/second, in particular from more than 150 to 200 meters/second and especially from 160 to 180 meters/second.

In one possible embodiment of the invention, it may be advisable to introduce the phosgene streams, especially the outer phosgene stream, into the mixing chamber with a higher flow rate than the amine stream that they surround, more preferably at least 10 m/s more, even more preferably at least 20 m/s more and especially at least 50 m/s more.

However, it may also be possible and advisable to introduce the outer phosgene stream into the mixing chamber with a higher flow rate than the amine stream, and the inner phosgene stream with a lower flow rate. This constitutes a further possible embodiment of the present invention.

In a preferred embodiment of the invention, it is advisable to introduce the phosgene streams, especially the outer phosgene stream, into the mixing chamber with a lower flow rate than the amine stream that they surround, more preferably at least 50 m/s less, even more preferably at least 60 m/s less, even more preferably 80 m/s less and especially at least 100 m/s less.

In a preferred embodiment of the present invention, in the case of a multitude of phosgene streams, these are connected to exactly one phosgene feed line with a low pressure drop and without additional regulating devices, such that the rate with which the phosgene flows is about the same.

Equally, in the case of a multitude of amine streams, they are preferably connected to exactly one amine line with a low pressure drop without additional regulating devices, such that the speed with which the amine flows is about the same.

However, it is also possible to connect the phosgene and/or amine streams in the slots to at least one separately regulated feed line each, such that the speeds are adjustable individually and independently of one another for each line.

The reactants enter the mixing chamber with a speed vector. The speed vector can be resolved into an axial, radial and tangential direction component. The axial direction is understood to mean the direction component of the speed vector parallel to the longitudinal axis of the mixing space. The radial direction is understood to mean the direction component of the speed vector from outside toward the longitudinal axis, i.e. enclosing a right angle with the longitudinal axis. Tangential direction is understood to mean the direction component of the speed vector parallel to the edge of the mixing chamber, i.e. a circular peripheral motion.

For the mixing of the reactant streams, an improvement in the mixing which is established can be achieved by the incorporation of elements which generate a tangential speed, for example into the feed line of the substreams of the excess components into the mixing chamber. A suitable tangential speed-generating element would, for example, be a spiral-twisted belt (helix) introduced into the feed line, round or rectangular guide plates (guide paddles) or the like. The action of the tangential speed-generating internals is to increase the shear between flow layers of different composition in the flow of the nozzle.

A further embodiment may also be constituted by providing the stream of the inert medium with a swirl. However, this is less preferred.

To generate a tangential speed, tangential entry of the feed line of one or more reactant streams is also possible, or, in the case of radial inflow of one or more reactant streams, a ring of paddles.

In addition, it may be advisable to introduce the phosgene and amine streams into the mixing chamber with contrarotatory tangential speed, for example by metering the phosgene streams into the mixing chamber with a clockwise tangential speed viewed along the longitudinal axis of the reactor, and the intervening amine stream with an anticlockwise tangential speed.

The angle enclosed by the cumulative vector formed from the vectors of the tangential speed and from the vector of the axial speed of the streams thus metered in enclosed with the longitudinal axis of the reactor may be from 5 to 85°, preferably from 17 to 73°, more preferably from 30 to 60° for one set of streams, for example the phosgene streams, and from −5 to −85°, preferably from −17 to −73°, more preferably from −30 to −60° for the other streams, for example the amine stream.

In addition, it is advisable to meter the flows into the mixing chamber with different radial speeds. In this case, an angle is established between the cumulative vector formed from the radial speed vector and from the axial speed vector with the longitudinal axis. This angle corresponds generally to the angle of the corresponding metering channel with the longitudinal axis of the mixing chamber. A negative angle means metered addition from the inside outward, a positive angle metered addition from the outside inward; an angle of 0° means a flow parallel to the longitudinal axis of the mixing chamber and an angle of 90° a flow at right angles to the longitudinal axis of the mixing chamber.

The outer phosgene stream can be metered into the mixing chamber through the mixing device at a radial angle of from 0 to 90°, preferably from 5 to 90°, more preferably from 7 to 65°, even more preferably from 15 to 35° and especially from 18 to 30°.

A preferred embodiment of the present invention is constituted by metering in the phosgene stream at an angle of about 90°, preferably exactly 90°, relative to the longitudinal axis of the mixing chamber, and the amine stream parallel longitudinal axis of the mixing chamber. In this case, the amine stream is enveloped by an inert medium, which is preferably metered in through an annular gap around the amine stream.

The amine stream can be metered into the mixing chamber at a radial angle of from −50° to +50°, preferably from −25 to 25°, more preferably from −10 to 10° and most preferably from −3 to +3°.

The inner phosgene stream can be metered into the mixing chamber through the mixing device at a radial angle of from 0 to −85°, preferably from −5 to −85°, more preferably from −7 to −65°, even more preferably from −15 to −35° and especially from −18 to −30°.

It is advantageous when the outer phosgene stream and amine stream, relative to one another, enclose a radial angle of from 1 to 60°, preferably from 7 to 50°, more preferably from 15 to 45° and more preferably from 18 to 35°.

It is also advantageous when the amine stream and inner phosgene stream, relative to one another, enclose a radial angle of from 1 to 60°, preferably from 10 to 50°, more preferably from 15 to 45° and more preferably from 18 to 35°.

In order to achieve substantially complete conversion of the amine to the particular product of value, a mixing time of the phosgene-containing stream with the amine-containing stream of less than 10 ms, preferably less than 5 ms, more preferably less than 2 ms, even more preferably less than 1 ms and especially less than 0.5 ms is achieved by the measures described above. The mixing time is defined as the maximum time needed by the fluid elements which exit from the amine feed until a phosgene/amine ratio of greater than or equal to 4 is established therein. The time is counted in each case from the exit of a fluid element out of the amine feed.

Reaction Chamber

The reaction chamber comprises, in the front region, the mixing chamber in which the mixing of the gaseous mixture of phosgene, amine, if appropriate mixed with inert medium, and separated by streams of inert medium, predominantly takes place, which is generally accompanied by the onset of the reaction. In the rear part of the reaction chamber, essentially only the reaction then takes place and, to a minor degree at most, the mixing.

For the purposes of distinction, the mixing chamber can refer to the region of the reaction chamber in which the mixing of the reactants takes place to a degree of 99%. In a preferred embodiment of the present invention, the conversion in the mixing chamber, i.e. the consumption of the amine used, is less than 15%. The degree of mixing is specified as the ratio of the difference of the locally averaged mixing ratio and of the starting mixing ratio before mixing relative to the difference of the mean final mixing ratio after mixing and of the initial mixing ratio before mixing. Regarding the concept of the mixing ratio, see, for example, J. Warnatz, U. Maas, R. W. Dibble: Verbrennung [Combustion], Springer Verlag, Berlin Heidelberg New York, 1997, 2nd edition, p. 134.

The effect of the inventive metered addition of the inert medium between an amine stream and a phosgene stream brings about merely reduced mixing of these two components in the region of the mixing device. At a particular distance from the mixing device, normal mixing of phosgene and amine then takes place.

Reactor is understood to mean the technical apparatus which comprises the reaction chamber. It may be all customary reaction chambers known from the prior art which are suitable for the noncatalytic, monophasic gas reaction, preferably for the continuous noncatalytic, monophasic gas reaction, and which withstand the moderate pressures required. Suitable materials for the contact with the reaction mixture are, for example, metals such as steel, tantalum, nickel, nickel alloys, silver or copper, glass, ceramic, enamel or homogeneous or heterogeneous mixtures thereof. Preference is given to using steel reactors. The walls of the reactor may be hydraulically smooth or profiled. Suitable profiles are, for example, cracks or waves.

It may be advantageous when the material used, preferably the material used for the mixing device and/or the reactor and more preferably that used for the reactor, has a low roughness, as described in unpublished European patent application 06125811.7 with the filing date Dec. 11, 2006, which is hereby incorporated fully in the context of the present disclosure by reference.

It is generally possible to use the reactor designs known from the prior art. Examples of reactors are known from EP-B1 289840, column 3 line 49-column 4 line 25, EP-B1 593334, WO 2004/026813, page 3 line 24-page 6, line 10, WO 03/045900, page 3 line 34-page 6 line 15, EP-A1 1275639, column 4 line 17-column 5 line 17, and EP-B1 570799, column 2 line 1-column 3 line 42, each of which is incorporated explicitly in the scope of this disclosure by reference.

Preference is given to using tubular reactors.

It is likewise possible to use essentially cuboidal reaction chambers, preferably plate reactors or plate reaction chambers. A particularly preferred plate reactor has a ratio of width to height of at least 2:1, preferably at least 3:1, more preferably at least 5:1 and especially at least 10:1. The upper limit in the ratio of width to height depends upon the desired capacity of the reaction chamber and is in principle not limited. Technically viable reaction chambers have been found to be those with a ratio of width to height up to 5000:1, preferably up to 1000:1.

The reaction of phosgene with amine in the reaction chamber is effected at absolute pressures of from more than 0.1 bar to less than 20 bar, preferably between 0.5 bar and 15 bar and more preferably between 0.7 and 10 bar. In the case of reaction of (cyclo)aliphatic amines, the absolute pressure is most preferably between 0.7 bar and 5 bar, in particular from 0.8 to 3 bar and especially from 1 to 2 bar.

In general, the pressure in the feed lines to the mixing apparatus is higher than the above-specified pressure in the reactor. According to the selection of the mixing apparatus, at this pressure declines. The pressure in the feed lines is preferably higher by from 20 to 2000 mbar, more preferably from 30 to 1000 mbar, than in the reaction chamber.

In one possible embodiment, the reactor consists of a bundle of reactors. In one possible embodiment, the mixing unit need not be an independent apparatus; instead, it may be advantageous to integrate the mixing unit into the reactor. One example of an integrated unit composed of mixing unit and reactor is that of a tubular reactor with flanged-on nozzles.

In the process according to the invention, the reaction of phosgene with amine is effected in the gas phase. Reaction in the gas phase is understood to mean that the conversion of the reactant streams and intermediates to the products react with one another in the gaseous state and, in the course of the reaction during passage through the reaction chamber, remain in the gas phase to an extent of at least 95%, preferably to an extent of at least 98%, more preferably to an extent of at least 99%, even more preferably to an extent of at least 99.5%, in particular to an extent of at least 99.8% and especially to an extent of at least 99.9%.

Intermediates are, for example, the monoamino monocarbamoyl chlorides, dicarbamoyl chlorides, monoamino monoisocyanates and monoisocyanato monocarbamoyl chlorides formed from the diamines, and also the hydrochlorides of the amino compounds.

In the process according to the invention, the temperature in the reaction chamber is selected such that it is above the boiling point of the diamine used, based on the pressure conditions existing in the reaction chamber. According to the amine used and pressure established, an advantageous temperature in the reaction chamber of more than 200° C., preferably more than 260° C. and more preferably more than 300° C. typically arises. In general, the temperature is up to 600° C., preferably up to 570° C.

The mean contact time of the reaction mixture in the process according to the invention is generally between 0.001 second and less than 5 seconds, preferably from more than 0.01 second to less than 3 seconds, more preferably from more than 0.015 second to less than 2 seconds. In the case of reaction of (cyclo)aliphatic amines, the mean contact time may even more preferably be from 0.015 to 1.5 seconds, in particular from 0.015 to 0.5 second, especially from 0.020 to 0.1 second and often from 0.025 to 0.05 second.

Mean contact time is understood to mean the time lapse from the beginning of mixing of the reactants until they leave the reaction chamber into the workup stage. In a preferred embodiment, the flow in the reactor of the process according to the invention is characterized by a Bodenstein number of more than 10, preferably more than 100 and more preferably of more than 500.

In a preferred embodiment, the dimensions of the reaction chamber and the flow rates are selected such that a turbulent flow is present for the reaction mixture, i.e. a flow with a Reynolds number of at least 2300, preferably at least 2700, the Reynolds number being formed with the hydraulic diameter of the reaction chamber.

The gaseous reaction mixture preferably flows through the reaction chamber with a flow rate of from 10 to 300 meters/second, preferably from 25 to 250 meters/second, more preferably from 40 to 230 meters/second, even more preferably from 50 to 200 meters/second, in particular from more than 150 to 190 meters/second and especially from 160 to 180 meters/second.

As a result of the turbulent flow, narrow residence time distributions with a low standard deviation of usually not more than 6%, as described in EP 570799, and good mixing are achieved. Measures, for example the constriction described in EP-A-593 334, which is additionally prone to blockage, are not necessary.

It may be advisable to incorporate flow homogenizers into the reactor, as known, for example, from EP 1362847A.

The reaction volume may be temperature-controlled over its outer surface. In order to build production plants with a high plant capacity, it is possible to connect a plurality of reactor tubes in parallel. However, the reaction can also preferably be effected adiabatically. This means that heating or cooling energy streams do not flow over the outer surface of the reaction volume by technical measures.

In a preferred embodiment, the reaction conditions are selected such that the reaction gas at the exit from the reaction chamber has a phosgene concentration of more than 25 mol/m$^3$, preferably from 30 to 50 mol/m$^3$. Moreover, at the exit from the reaction chamber, an inert medium concentration of more than 25 mol/m$^3$, preferably of from 30 to 100 mol/m$^3$, is generally present.

The reaction chamber may have a uniform diameter or have a series of constrictions or widenings in the course of the flow. This is described, for example, in WO 2007/028715, page 14 line 29 to page 20 line 42, which is hereby explicitly incorporated into the present disclosure.

However, the configuration of the reaction chamber, in accordance with the invention, does not play any role in the mixing of the components.

The volume of the reactor which is flowed through can be filled with static mixers, for example structured packings, random packings, fabrics, perforated or slotted sheets; however, the volume is preferably very substantially free of internals.

The installation of guide plates into the reaction chamber is also conceivable. A suitable turbulence-generating element would, for example, be an inserted spiral-twisted belt, round or angular oblique plates or the like.

In order to maintain short mixing path lengths and hence short mixing times even in the case of large amine and phosgene flow rates, as customary in isocyanate production on the industrial scale, one possibility is parallel connection of many small mixing nozzles with an adjoining mixing and reaction zone, in which case the parallel-connected units are separated from one another by walls. The advantage of this process variant lies in a relatively favorable length to diameter ratio of the mixing and reaction zones. The larger this ratio is, the more favorable (narrower) is the residence time distribution of the flow. At the same residence time and flow rate, it is thus possible by virtue of many parallel-connected units that the length to diameter ratio is increased and hence the residence time distribution is also narrowed. In order to minimize the apparatus complexity, the individual reaction zones open into a combined postreaction zone, in which the remaining conversion of the amine is effected.

Quench

After the reaction, the gaseous reaction mixture is washed with a solvent, preferably at temperatures greater than 130° C. (quench). Preferred solvents are hydrocarbons which are optionally substituted by halogen atoms, for example hexane, benzene, nitrobenzene, anisole, chlorobenzene, chlorotoluene, o-dichlorobenzene, trichlorobenzene, diethyl isophthalate (DEIP), tetrahydrofuran (THF), dimethylformamide (DMF), xylene, chloronaphthalene, decahydronaphthalene and toluene. The solvent used is more preferably monochlorobenzene. The solvent used may also be the isocyanate. In the wash, the isocyanate is transferred selectively to the wash solution. Subsequently, the remaining gas and the resulting wash solution are separated, preferably by means of rectification, into isocyanate, solvent, phosgene and hydrogen chloride.

Once the reaction mixture has been converted in the reaction chamber, it is conducted into the workup apparatus with quench. This is preferably a so-called wash tower, wherein the isocyanate formed is removed from the gaseous mixture by condensation in an inert solvent, while excess phosgene, hydrogen chloride and, if appropriate, the inert medium pass through the workup apparatus in gaseous form. Preference is given to keeping the temperature of the inert solvent above the dissolution temperature of the carbamoyl chloride corresponding to the amine in the selected quench medium. Particular preference is given to keeping the temperature of the inert solvent above the melting point of the carbamoyl chloride corresponding to the amine.

In general, the pressure in the workup apparatus is lower than in the reaction chamber. The pressure is preferably lower by from 50 to 500 mbar, more preferably from 80 to 150 mbar, than in the reaction chamber.

The wash can, for example, be carried out in a stirred vessel or in other conventional apparatus, for example in a column or mixer-settler apparatus.

In process technology terms, it is possible to use all extraction and washing processes and apparatus known per se for a wash in the process according to the invention, for example those which are described in Ullmann's Encyclopedia of Industrial Chemistry, 6th ed, 1999 Electronic Release, chapter: Liquid—Liquid Extraction—Apparatus. For example, these may be one-stage or multistage, preferably one-stage, extractions, and also those in cocurrent or countercurrent mode, preferably countercurrent mode.

The quench may, for example, be designed as described in EP 1403248 A1, and there particularly in paragraphs [0006] to [0019] and the example together with FIGS. 1 and 2, which is hereby incorporated in the present disclosure by reference.

The quench may, for example, be designed as described in WO 2008/55899, and there particularly from page 3 line 30 to page 11 line 37, together with example 1 and the figures, which is hereby incorporated in the present disclosure by reference.

The quench may, for example, be designed as described in WO 2008/55904, and there particularly from page 3 line 26 to page 16 line 36, together with example 1 and the figures, which is hereby incorporated in the present disclosure by reference.

The quench may preferably be designed as described in WO 2005/123665, and there particularly from page 3 line 10 to page 8 line 2 and the example, which is hereby incorporated in the present disclosure by reference.

In this quench zone, the reaction mixture, which consists essentially of the isocyanates, phosgene and hydrogen chloride, is mixed intensively with the liquid sprayed in. The mixing is effected by lowering the temperature of the reaction mixture proceeding from 200 to 570° C. to from 100 to 200° C., preferably to from 140 to 180° C., and transferring the isocyanate present in the reaction mixture completely or partly by condensation into the liquid droplets sprayed in, while the phosgene and the hydrogen chloride remain essentially completely in the gas phase.

The proportion of the isocyanate present in the gaseous reaction mixture which is transferred into the liquid phase in the quench zone is preferably from 20 to 100% by weight, more preferably from 50 to 99.5% by weight and especially from 70 to 99% by weight, based on the isocyanate present in the reaction mixture.

The reaction mixture preferably flows through the quench zone from the top downward. Below the quench zone is arranged a collecting vessel in which the liquid phase is separated out, collected, removed from the reaction chamber via an outlet and then worked up. The remaining gas phase is removed from the reaction chamber via a second outlet and likewise worked up.

The quench can be effected, for example, as described in EP 1403248 A1 or as described in international application WO 2005/123665.

To this end, the liquid droplets are generated by means of one-substance or two-substance atomizer nozzles, preferably one-substance atomizer nozzles, and, according to the embodiment, generate a spray cone angle of from 10 to 140°, preferably from 10 to 120°, more preferably from 10° to 100°.

The liquid which is sprayed in via the atomizer nozzles must have a good solubility for isocyanates. Preference is given to using organic solvents. In particular, aromatic solvents which may be substituted by halogen atoms are used.

In a particular embodiment of the process, the liquid sprayed in is a mixture of isocyanates, a mixture of isocyanates and solvent, or isocyanate, in which case the quench liquid used in each case may have proportions of low boilers, such as HCl and phosgene. Preference is given to using the isocyanate which is prepared in the particular process. Since the lowering of the temperature in the quench zone causes the reaction to stop, side reactions with the isocyanates sprayed in can be ruled out. The advantage of this embodiment is especially that removal of the solvent can be dispensed with.

In an alternative preferred embodiment, the inert medium which is used together with at least one of the reactants and the solvent which is used in the quench are the same compound; in this context, very particular preference is given to using monochlorobenzene.

Small amounts of by-products which remain in the isocyanate can be separated from the desired isocyanate by means of additional rectification, by stripping with an inert gas or else crystallization, preferably by rectification.

In the subsequent optional purification stage, the isocyanate is removed from the solvent, preferably by distillation. It is likewise possible here to remove residual impurities, comprising hydrogen chloride, inert medium and/or phosgene, as described, for example, in DE-A1 10260092.

EXAMPLE

In a Miniplant system for gas phase phosgenation of 1,6-hexamethylenediamine to 1,6-hexamethylene diisocyanate, 1.77 kg/h of a mixture of 99.2% by weight of 1,6-hexamethylenediamine and 0.8% by weight of nitrogen were heated to 365° C. and mixed in a coaxial mixing nozzle with 15 kg/h of phosgene with a temperature of 365° C. The opening of the central amine feed had a diameter of 1.0 mm, and the phosgene was fed through an annular gap of 3 mm into a mixing tube of diameter 5.2 mm.

In the course of operation of the system, a rise in the pressure drop occurred after only a few minutes, which was attributable to deposits in the nozzle region and ultimately led to the shutdown of the plant.

In accordance with the invention, an annular gap of 1 mm for the metered addition of approx. 0.35 kg/h of nitrogen as an inert medium was then installed between the central amine orifice and the phosgene gap. The system was then operated over several hours without a significant rise in pressure drop. After deinstallation and dismantling of the nozzles, no deposits were found in the region of the mixing zone.

LIST OF REFERENCE NUMERALS

1 Amine stream
2 Phosgene stream
3 Inert medium
4 Reaction mixture
5 Inert medium

The invention claimed is:

1. A process for preparing an isocyanate, the process comprising:
contacting fluid streams of amine, phosgene and inert medium in at least one mixing device, such that an inert medium stream is metered at least between one amine stream and one phosgene stream within the mixing device; and then
reacting an amine with phosgene to form an isocyanate, wherein:
the inert medium stream is metered such that a point of first contact of the amine and the phosgene occurs at a distance from a surface of the mixing device;
a perpendicular phosgene stream is metered at an angle of about 90° relative to a longitudinal axis of a mixing chamber of the mixing device;
a parallel amine stream is metered at an orientation parallel to the longitudinal axis of the mixing chamber; and one inert medium stream is metered into the parallel amine stream on a side of a parallel amine flow channel facing the perpendicular phosgene stream.

2. The process according to claim 1, wherein one inert medium stream is metered in between one amine stream and two phosgene streams.

3. The process according to claim 2, wherein one inert medium stream is metered into the phosgene stream on a side of phosgene stream channels facing the amine stream.

4. The process according to claim 2, wherein the inert medium stream is metered into the amine stream on sides of an amine flow channel facing the phosgene stream.

5. The process according to claim 1, wherein an additional inert medium stream is metered in between a phosgene stream and a wall of the mixing device.

6. The process according to claim 1, wherein the mixing device is an annular gap mixing nozzle.

7. The process according to claim 1, wherein the mixing device is a slot nozzle.

8. The process according to claim 1, wherein mixing is effected in at least one mixing apparatus selected from the group consisting of a coaxial mixing nozzle, a Y mixer, a T mixer, a jet mixer and a mixing tube.

9. The process according to claim 1, wherein the inert medium is selected from the group consisting of nitrogen, helium, argon, chlorobenzene, chlorotoluene, o-dichlorobenzene, toluene, xylene, chloronaphthalene, decahydronaphthalene, carbon dioxide and carbon monoxide.

10. The process according to claim 1, wherein the mixing device comprises three-substance mixing nozzles for metered addition of the fluid streams of amine, phosgene and inert medium in a gas phase phosgenation.

11. The process according to claim 1, wherein the mixing device comprises three-substance mixing nozzles for metered addition of the fluid streams of amine, phosgene and inert medium in a liquid phase phosgenation.

12. The process according to claim 1, wherein the inert medium stream is metered such that a point of first contact of amine of the one amine stream and phosgene of the one phosgene stream occurs at a distance from a surface of the mixing device, such that deposition of a blocking solid on the surface of the mixing device is reduced or suppressed.

13. The process according to claim 1, wherein a ratio of absolute speeds of the inert medium stream to the phosgene stream at a point of contact of the streams is in a range from 2:1 to 1:2.

14. The process according to claim 1, wherein a ratio of absolute speeds of the inert medium stream to the amine stream at a point of contact of the streams is in a range from 2:1 to 1:2.

15. The process according to claim 1, wherein a speed difference of absolute speeds of the inert medium stream and the phosgene stream is less than 10 m/s.

16. The process according to claim 1, wherein a ratio of gas volumes of the inert medium to the amine or the phosgene is less than 1.

17. The process according to claim 1, wherein a ratio of an area of the inert medium stream to a total area of an adjacent amine stream or an adjacent phosgene stream is greater than 0.0002 and up to 5.

* * * * *